United States Patent
Williams et al.

[11] Patent Number: 6,132,473
[45] Date of Patent: Oct. 17, 2000

[54] DIFFERENTIAL TREATMENT OF PROSTHETIC DEVICES

[75] Inventors: R. Brian Williams, Eagan; Richard F. Schroeder, Oakdale; Matthew F. Ogle, St. Paul, all of Minn.

[73] Assignee: St. Jude Medical, Inc., St. Paul, Minn.

[21] Appl. No.: 09/086,193

[22] Filed: May 28, 1998

Related U.S. Application Data

[62] Division of application No. 08/850,812, May 2, 1997.

[51] Int. Cl.⁷ ................................................. A61F 2/02
[52] U.S. Cl. ......................................... 623/66.1; 623/2.1
[58] Field of Search ........................... 623/66, 1, 2, 11, 623/12; 8/94.11

[56] References Cited

U.S. PATENT DOCUMENTS

| | | |
|---|---|---|
| 3,966,401 | 6/1976 | Hancock et al. . |
| 4,247,292 | 1/1981 | Angell . |
| 4,372,743 | 2/1983 | Lane . |
| 4,800,603 | 1/1989 | Jaffe . |
| 5,279,612 | 1/1994 | Eberhardt . |
| 5,613,982 | 3/1997 | Goldstein .................................. 623/11 |

FOREIGN PATENT DOCUMENTS

| | | |
|---|---|---|
| 0 570 331 | 11/1993 | European Pat. Off. . |
| WO 93 04643 | 3/1993 | WIPO . |
| WO 96 08213 | 3/1996 | WIPO . |

OTHER PUBLICATIONS

Medtronic Informational Brochure, "The Freestyle Aortic Root Bioprosthesis".

*Primary Examiner*—David J. Isabella
*Attorney, Agent, or Firm*—Westman, Champlin & Kelly, P.A.; Peter S. Dardi; Hallie A. Finucane

[57] ABSTRACT

An apparatus is disclosed for differentially treating a medical device. One portion of the device is treated with a first fluid and a separate portion is treated with a second fluid. The second fluid generally is substantially different from the first fluid. The first fluid can be contacted with an flow region of the medical device. The apparatus can include a conduit system, where fluid flowing through the conduit system flows through the flow region. Sheet material can be treated differentially on the opposite surfaces of the sheet. The medical device can include vascular tissue.

20 Claims, 5 Drawing Sheets

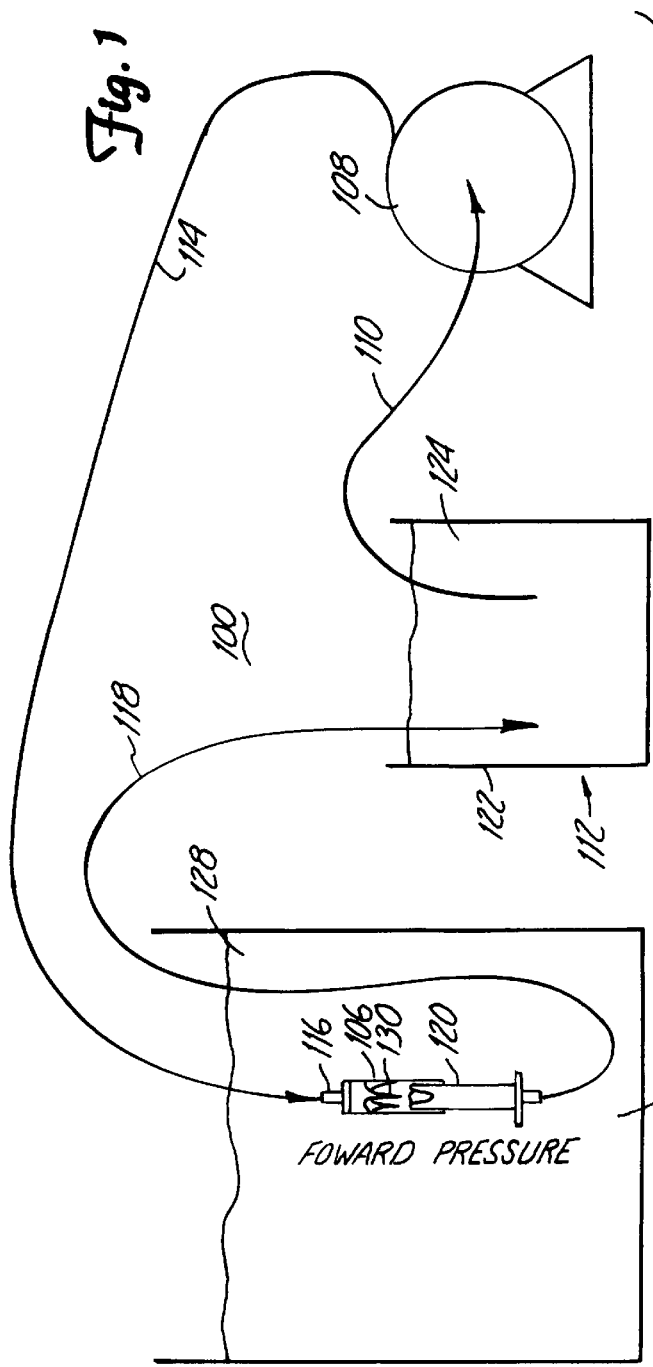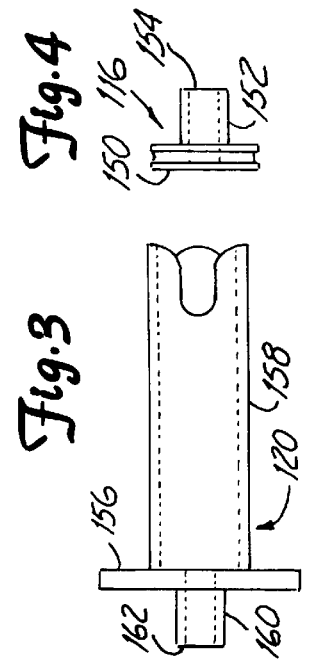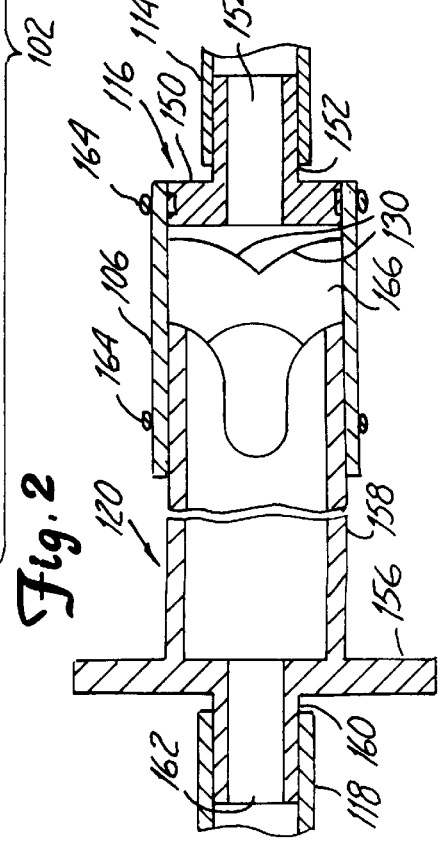

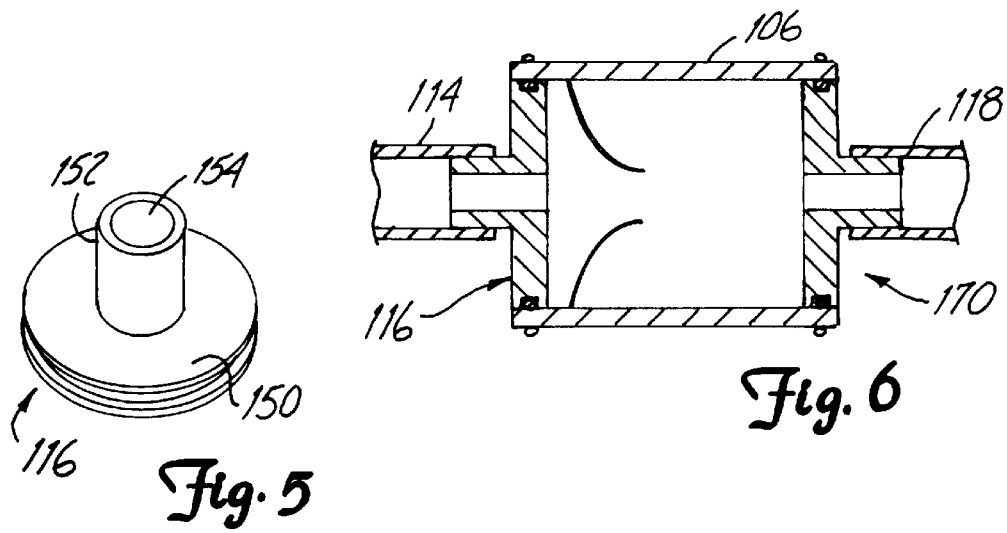
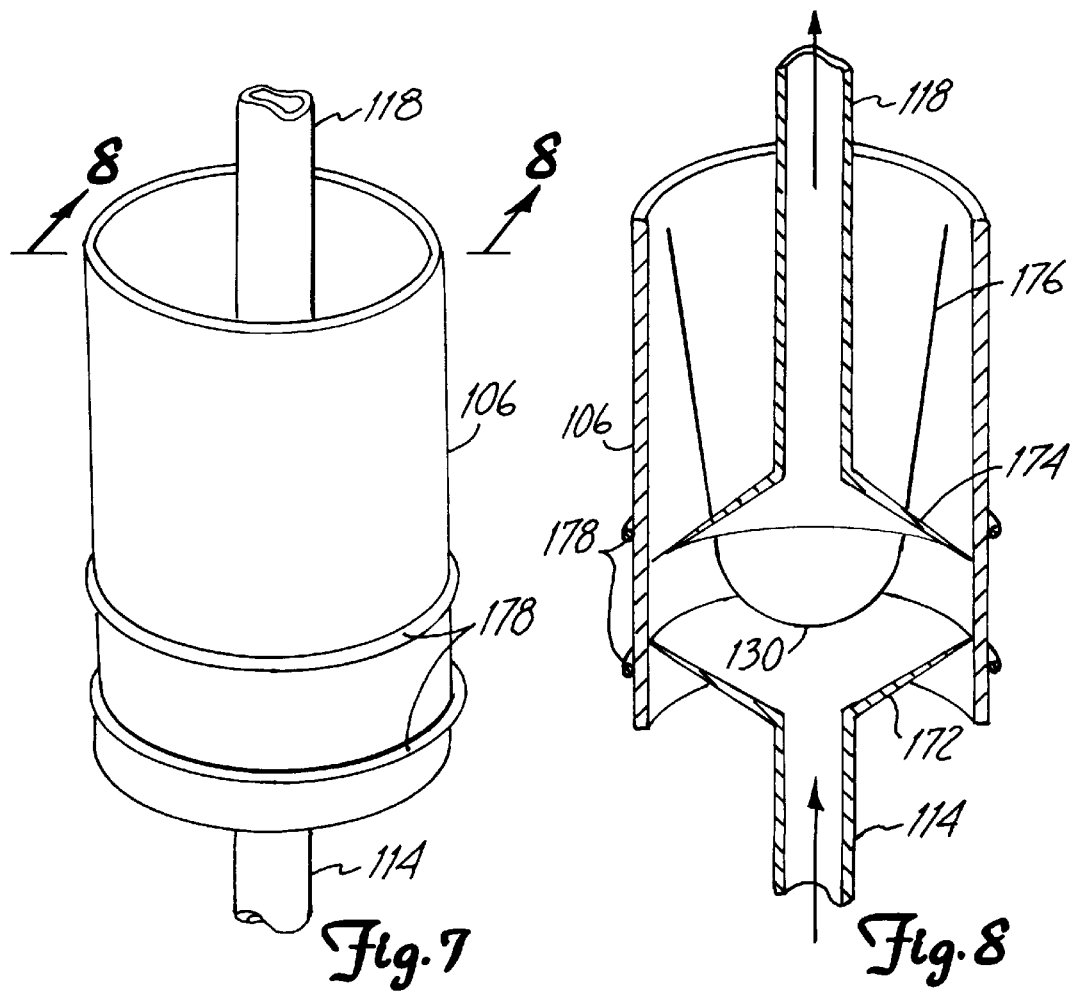

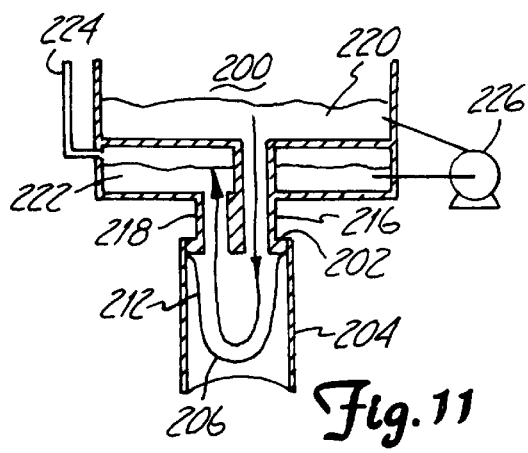
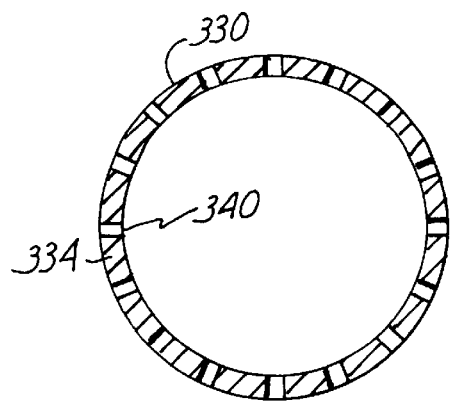
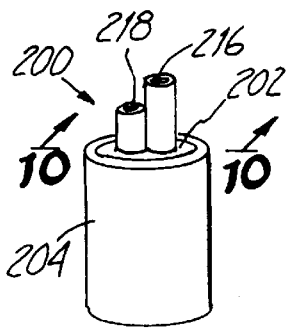
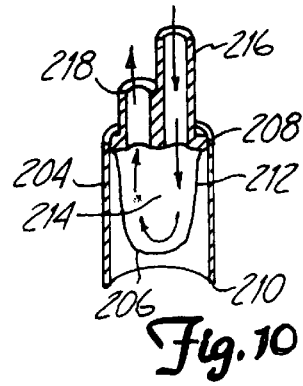
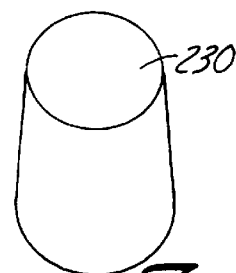
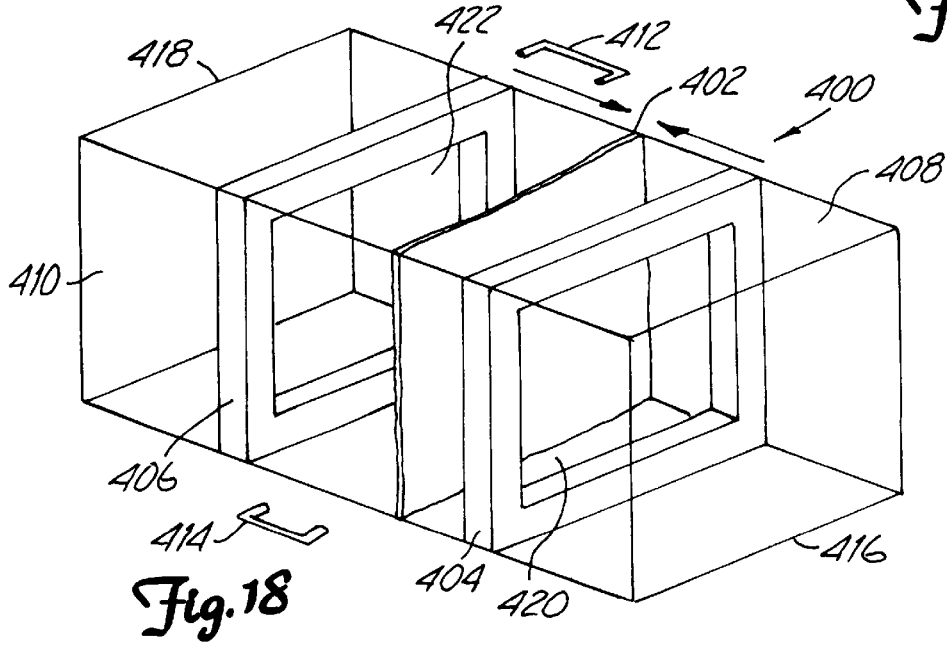

DIFFERENTIAL TREATMENT OF PROSTHETIC DEVICES

CROSS REFERENCE TO RELATED APPLICATIONS

This application is a divisional of U.S. patent application Ser. No. 08/850,812.

FIELD OF THE INVENTION

The invention relates to the treatment of separate portions of medical devices such as bioprosthetic devices, with selected, different treatment solutions.

BACKGROUND OF THE INVENTION

A variety of medical devices such as prostheses can be used to repair or replace damaged or diseased organs, tissues and other structures in humans and animals. Some of these medical devices incorporate tissue or synthetic material as at least a component of the prosthesis. Prostheses generally must be biocompatible due to possible prolonged contact with bodily fluids.

It is often necessary or desirable to treat the natural or synthetic tissue prior to use to improve performance of the prosthetic. Tissue used in prostheses typically is fixed prior to use. Fixation stabilizes the tissue, especially from enzymatic degradation, and reduces antigenicity.

In addition, a prosthesis can be treated with a variety of agents to reduce calcification, i.e., the deposit of calcium salts, particularly calcium phosphate (hydroxyapatite), following implantation in a recipient. Calcification affects the performance and structural integrity of medical devices constructed from these tissues, especially over extended periods of time. For example, calcification is the primary cause of clinical failure of bioprosthetic heart valves. The tissue can also be decellularized in an effort to reduce the effects of calcification and to promote cell growth. Other possible treatments include the application of, for example, antimicrobials, antioxidants and antithrombotics.

Some treatments for medical devices involve the use of potent chemicals, which can result in degradation of delicate portions of the medical device. Also, treatments beneficial to one portion of a medical device may be detrimental to another portion of the bioprosthesis. Furthermore, certain treatments may be appropriate for one portion of a medical device but not other portions due to differences in material or due to the different environments to which the different portions of the medical device may be exposed during use.

SUMMARY OF THE INVENTION

The present invention provides for the treatment of different portions of a medical device with different treatment solutions. Therefore, delicate parts of a device can be protected while treating other, less sensitive parts with relatively potent but beneficial treatment solutions. In addition, different portions of a medical device may be in different environments following implantation into a patient. These different portions can be prepared in different ways in preparation for exposure to the different environments. Other advantages of the invention are evident from the description below.

In a first aspect, the invention features an apparatus including:

(a) a first fluid applicator for contacting a first portion of a medical device with a first fluid; and (b) a second fluid applicator for contacting a second portion of the medical device with a second fluid, the second fluid applicator applying the second fluid in effective isolation from the first portion of the medical device and the first fluid applicator applying the first fluid in effective isolation from the second portion of the medical device.

In some embodiments, the first fluid applicator includes a fluid conduit system including a support system for attaching the fluid conduit system to the medical device such that when attached to the device, fluid flowing through the conduit system contacts a flow region. The support system of the apparatus can include a support that inserts within an opening in the tissue, where the support has a passageway such that fluid flowing through the conduit system flows through the passageway and contacts the first portion of the tissue. The treatment fluid can include a liquid bath, a liquid spray, an aerosol, a gas or a combination thereof.

The apparatus can further include a fastener that holds the tissue against the supports. The fluid applicator can include a container for holding a fluid into which the tissue attached to the conduit system is immersed. In another embodiment, the fluid applicator includes a porous member that direct streams of liquid at the tissue attached to the conduit system.

In another embodiment, the apparatus includes a frame that holds a sheet section of a medical device to facilitate the application of the second fluid in effective isolation from the first portion of the medical device. The first portion can be one side of said sheet section. The second portion can be a side of the sheet opposite the first portion.

In another aspect, the invention features a method of treating a medical device including the steps of:

(a) contacting a first portion of the device with a first fluid such that a second portion of the device is not significantly contacted by the first fluid; and (b) contacting the second portion of the device with a second fluid substantially different from the first fluid such that the first portion of the device is not significantly contacted by the second fluid.

In some embodiments, the contacting of said first portion involves flowing a first fluid through a fluid conduit system attached to the device such that the fluid flowing through the conduit system contacts the first portion of the device. The fluid conduit system can include a support that inserts within an opening in the device, where the support has a passageway such that fluid flowing through the conduit system flow through the passageway and contacts the first portion of the device.

In the method of treating the device, the contacting of the second portion can be performed by surrounding the tissue with the second fluid, where the second fluid includes a liquid. In an alternative embodiment, the contacting of the second portion is performed by spraying the second portion of the device with the second fluid, where the second fluid can be a liquid. In another alternative embodiment, the contacting step is performed by surrounding the device with the second fluid, where the second fluid includes a gas.

In another aspect, the invention features an isolated, i.e., ex vivo, vascular tissue including a first region treated with a surface modifying composition and a second region substantially devoid of modification by the surface modifying composition. The surface modifying composition can include, for example, a calcification inhibiting composition such as polyvalent metal cations, an antimicrobial composition, a fixation composition, and/or a decellularization composition such as a composition of digestive enzymes. The first region and/or the second region can be a flow region. Alternatively, the first and second regions can be opposite sides of a sheet material.

In another aspect, the invention features a vascular tissue having an outer decellularized portion and an inner portion substantially devoid of decellularization.

In another aspect, the invention features a vascular tissue having an outer decellularized portion and an inner decellularized portion comprising leaflets, said leaflets substantially maintaining the mechanical properties of the native leaflets.

BRIEF DESCRIPTION OF THE DRAWINGS

FIG. 1 is a schematic representation of an apparatus of the invention.

FIG. 2 is a sectional view of a first support and a second support of the apparatus of FIG. 1 attached to a medical device, where the cross section is taken through the axis passing through the center of the supports.

FIG. 3 is a side view of the first support of the apparatus of FIG. 1 with internal passages indicated with dotted lines.

FIG. 4 is a side view of the second support of the apparatus of FIG. 1 with an internal passage indicated with a dotted line.

FIG. 5 is a perspective view of the second support of FIG. 1.

FIG. 6 is a sectional view of an alternative embodiment of a support system, where the section is taken through the axis running through the center of the supports.

FIG. 7 is a perspective view of another alternative embodiment of a support system attached to a medical device.

FIG. 8 is a sectional view of the support system of FIG. 7 taken along lines 8—8 of FIG. 7.

FIG. 9 is a fragmentary, perspective view of an alternative embodiment of the fluid conduit system attached to a medical device.

FIG. 10 is a fragmentary, sectional view of the fluid conduit system of FIG. 9 taken along lines 10—10 of FIG. 9.

FIG. 11 is a sectional view of the fluid conduit system of FIG. 9 taken along the same view as FIG. 10.

FIG. 12 is a perspective view of a plug that can be used along with the fluid conduit system of FIG. 9.

FIG. 13 is a perspective view of a skirt that can be used along with the fluid conduit system of FIG. 9.

FIG. 17 is a sectional view of the sprayer of FIG. 15 taken along lines 17—17 of FIG. 15.

FIG. 18 is a perspective view of an alternative embodiment of the invention for the differential treatment of a device including a portion of sheet material, where the container is displayed as transparent.

DESCRIPTION OF THE PREFERRED EMBODIMENTS

Figure 14:
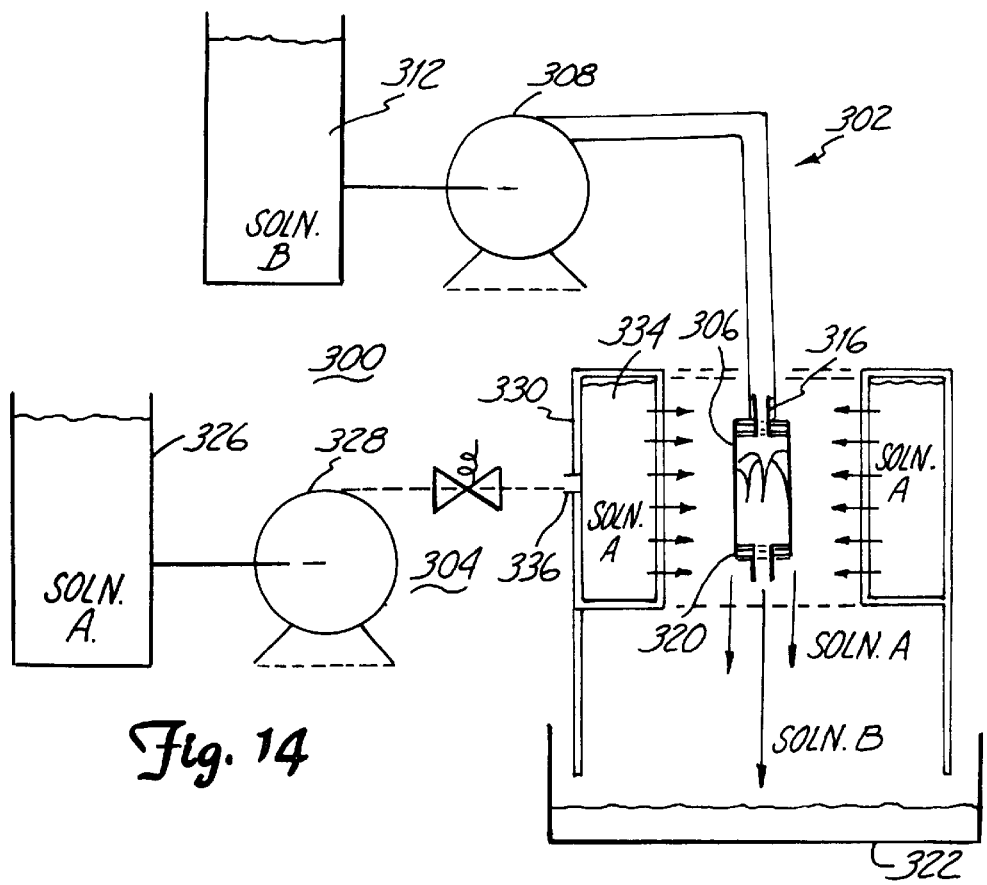
FIG. 14 is a schematic representation of an alternative embodiment of an apparatus of the invention.
Figure 15:
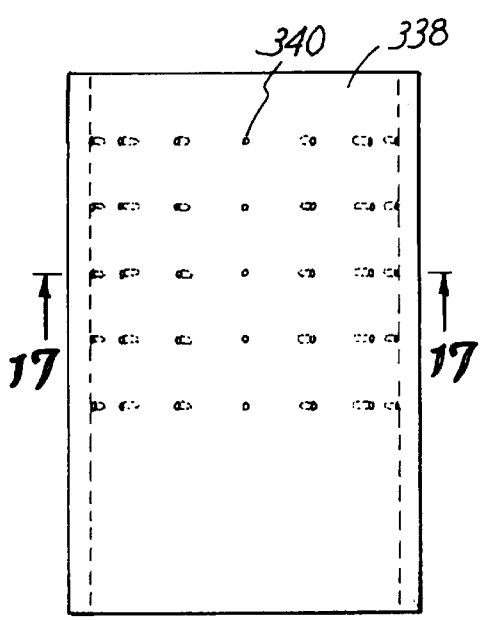
FIG. 15 is a side view of a sprayer of the apparatus of FIG. 14.

The invention is directed toward differential treatment of portions of medical devices that are made, at least in part, with tissue or appropriate synthetic materials. Under the differential treatment, two or more portions of the device are subjected to different fluid treatments. Since some desirable treatments require potent chemicals, particularly sensitive portions of a medical device can be protected from the chemicals using differential treatments. In addition, it may be desirable to treat separate portions of a prosthesis or other medical device in different ways because the separate portions are exposed to different environments in use. The differential treatment can impart to the appropriate portions of the device the desired characteristics for the different environments.

The device is contacted at one portion with a first fluid and at a separate portion with a second fluid. These portions may or may not together include the entire surface of the device. A separate third portion can also be treated with a third fluid, and similarly with additional portions.

An apparatus is described to perform the differential treatment. In some preferred embodiments, the apparatus includes a conduit system that connect to a flow region such that fluid flowing through the conduit system flows through the flow region of the device. The second fluid can be applied in relative isolation from the flow region. In other preferred embodiments, two different fluids are applied to opposite sides of a sheet material.

Medical Devices

Appropriate medical devices for treatment include, for example, prostheses, components of prostheses or material to be fabricated into a prosthesis. The device generally has one contact surface that functions differently in use than another contact surface. A contact surface can include, for example, a flow region, a sheet region or both flow and sheet regions. Examples of materials with sheet regions include patches such as pericardial patches and skin grafts.

Examples of materials with flow regions include vascular tissue, GI track repair material, lymphatic ducts, nerve repair channels, urinary tract repair material and bronchial tubes. Vascular tissue includes, for example, heart valves, vascular grafts, valved vascular grafts, biological conduits and valved biological conduits such as valved pulmonary conduits. With vascular tissue, the flow region generally includes all or a portion of the region that would be in contact with the vascular flow when in use. Sections of the structure involving the natural vascular flow may be isolated from the flow region because of the location of attachment of a conduit system of the apparatus to the device. For treatment, natural tissues are isolated from the source animal for attachment to one of the various embodiments of the apparatus described below.

Appropriate devices can be made from natural material, synthetic material or a combination of natural and synthetic material. Appropriate natural materials include, for example, tissues. The tissue may have an intrinsic portion identifiable as a natural flow region, or the flow region may be formed upon fabrication of the tissue into an appropriate device or component of a device. Alternatively, the device may be used as a sheet having two contact surfaces, each requiring different properties.

Appropriate tissues include intact tissue as well as decellularized tissue. These tissues may be obtained from, for example, natural heart valves; portions of natural heart valves such as roots, walls and leaflets; pericardial tissues such as pericardial patches; connective tissues; bypass grafts; tendons; ligaments; skin patches; blood vessels; cartilage; dura matter; skin; bone; umbilical tissues; GI tract tissues; and the like.

Natural tissues are derived from a particular animal species such as shark, lizard and, typically but not limited to mammalian, such as human, bovine, porcine, seal or kangaroo. These natural tissues generally include collagen-containing material. Natural tissue is typically, but not necessarily, soft tissue. As a specific example, pericardial tissue can be formed into a variety of vascular devices such as valved conduits.

Appropriate tissues also include tissue equivalents such as a tissue-engineered material involving a cell-repopulated matrix, which can be formed from polymers, biopolymers or from a decellularized natural tissue. Biopolymers can be naturally occurring or produced in vitro by, for example, fermentation and the like. Purified biopolymers can be appropriately formed into a substrate by techniques such as weaving, knitting, casting, molding, extrusion, cellular alignment and magnetic alignment.

Synthetic components of the prosthesis can be formed from a variety of biocompatible materials such as metals, polymers, ceramics and combinations thereof. Appropriate polymers include, for example, hydrogels, reabsorbable polymers and nonreabsorbable polymers.

Devices made exclusively from synthetic materials include, for example, annuloplasty rings, heart valve cuffs and prosthetic valved vascular grafts such as an aortic valved graft for ascending aortic reconstruction. The vascular portion of the graft preferably is made from, for example, polymer material such as woven poly(ethylene terephthalate) and polytetrafluoroethylene. The valves can be mechanical valves preferably made from metal, polymers such as solid or extruded polymers, ceramics or combinations thereof.

Synthetic components also can take the form, for example, of stents, cloth covers, sewing cuffs and/or suture. These can be combined with other natural or synthetic components.

Apparatus

The apparatus includes a first fluid applicator and a second fluid applicator. The fluid applicators are configured to administer different fluids to separate portions of the medical device. Additional fluid applicators can be used, if desired, to deliver additional different fluids. Preferably, the different fluids are applied simultaneously, at least for a portion of their respective application times. While not preferred, a single fluid applicator can be used that is moved from one location to another to apply different fluids to separate portions of the medical device.

The fluids can be applied in a variety of forms, for example a liquid bath, a gas, and/or an aerosol spray. Preferably, one of the fluids is applied as a liquid spray. Use of a liquid spray provides for adequate contact with the liquid while minimizing the opportunity for flow of the liquid to other portions of the medical device. Furthermore, the use of a spray can reduce cost by controlling application rate, can control depth of penetration by varying gradients and can speed manufacturing time by increasing pressure gradients.

The appropriate structure for a fluid applicator follows from the type of fluid to be applied. If the fluid is a liquid bath, the fluid applicator can be a container with fluid. If the fluid is a liquid or a gas and the portion of the device is a flow region, the fluid applicator can be a conduit system isolating the flow region. The device attached to a conduit system to isolate a flow region can be immersed into a liquid bath in a container for the amount of time desired for treatment. Similarly, if the fluid is a gas, the fluid applicator can be a container holding the gas at an appropriate pressure. A device attached to a conduit system can be placed within the gas container for an appropriate period of time. Sufficient contact with a fluid can be determined empirically based on the desired properties of the treated device.

In some embodiments, the separate portions of the medical device to be differentially treated are two sides of a sheet section of material forming the medical device or a portion of the medical device. For these embodiments, the apparatus preferably includes a frame that holds the material to facilitate the differential treatment of the two sides and minimizes the risk of fluid flow from one side of the material to the other. The specific fluid applicators can be configured on each side of the frame and have the appropriate form for the type of fluid to be applied, as described above. A device can have sheet portions and other portions where the differential treatment involves treatment of one side of the sheet portion with one fluid and another portion of the device with another fluid.

In some embodiments of the apparatus, one of the fluid applicators includes a fluid conduit system that attaches to the device for isolating a first portion of the medical device, i.e., the flow region. Generally, a first fluid flows through the conduit system and contacts the flow region. In these embodiments, the apparatus also includes another fluid applicator for contacting a second portion of the device with a second fluid in effective isolation from the flow region.

The conduits generally include a pressure gradient applying device (e.g., a pump, a gravity feed, a pressurized gas cylinder or the like), tubing, a fluid source and a support system for attaching the conduits to the device for treatment. If the pressure gradient applying device is a pump, the pump can be of any design with peristaltic pumps being preferred to prevent contamination of the fluid. The tubing is preferably inert with respect to any fluid to be flowed through the tubing. The tubing can be made from any suitable material, and preferred materials for the tubing include stainless steel and vinyl polymers such as Tygon$^R$ (Norton Performance Plastics Corp., Akron, Ohio) and polytetrafluoroethylene. The fluid source generally is a container suitable to hold the particular type of fluid. A fluid source may not be needed if sufficient fluid is otherwise circulating through the conduit system.

The support system preferably includes one or more supports that are secured within an opening of the device. A support can have a variety of shapes such as those described below with respect to the figures. Tension alone may be sufficient to secure the support to the device. Alternatively, a fastener can be placed over the device at or near the location of the support to secure the device on the support. The fastener can be made of any of a variety of materials such as metal, ceramics, natural or synthetic polymers or combinations thereof. The fastener can comprise sutures appropriately passed through the device. Alternatively, the fastener can be a simple thread tied around the device or can be a more elaborate adjustable clamp that releasably attaches to the device. Other alternatives for the fastener include, for example, ties, clips, polymer bands and staples.

Two supports can be attached respectively within two openings of the device. Each support has a passageway, generally through the middle of the support. The flow region is located between the two points of attachment of the supports. Fluid flowing through one section of tubing flows through the passageway of one support, through the flow region of the device, through the passageway of the second support and into another section of tubing. If only one support is used, fluid flowing through the flow region of the device exits through an opening in the device and generally flows to a collection container.

There may be some leakage between the flow region and the exterior of the flow region. For example, aortic heart valves have coronary arteries branching off the main vessel. These arteries may be tied off, but they may still leak a small amount. Some leakage generally is not detrimental since any fluid that leaks from one region to another generally is diluted by fluid in the second region. This substantial dilution prevents any significant effect from the leaking fluid. Preferably, the fluid applied at the second portion of the device has a neutralizing or inactivating effect to inhibit the activity of the leaking fluid, as discussed further below.

Similarly, some fluid may leak into the flow region following application by the fluid applicator. This leakage generally is diluted and/or inactivated by the flow within the flow region. As long as the leaking fluid is sufficiently diluted/inactivated and removed by the flow in the flow region, no discernable modification of the flow region of medical device results from the leakage. The apparatus generally can be designed so that pressure gradients provide a pressure barrier affording additional protection of selected portions of the medical device by resisting flow of the undesired fluid to the protected portions. In addition, small amounts of leakage from one region to another generally do not have significant effects even without dilution or inactivation by another fluid.

An embodiment of the apparatus is depicted in FIG. 1. Apparatus 100 includes fluid conduit system 102, fluid applicator 104 and device 106. Fluid conduit system 102 includes a peristaltic pump 108 connected by tubing 110 to a first fluid source 112 and by tubing 114 to a first support 116. Tubing 118 connects fluid source 112 to a second support 120. Fluid source 112 includes a container 122 holding first fluid 124. Fluid applicator 104 includes a container 126 holding second fluid 128. Apparatus 100 can be used with any appropriate vascular tissue or device. Device 106 is depicted in FIG. 1 with the outer portion transparent such that leaflets 130 of a valve within the device can be seen.

Referring to FIGS. 2, 4 and 5, first support 116 has a disc section 150 that fits into one end of device 106. Projection 152 provides for attachment of tubing 114 to support 116. Passageway 154 extends through the projection 152 to provide fluid communication between the two sides on support 116.

Referring to FIG. 2 and 3, second support 120 has an enlarged disc 156 from which a cylindrical section 158 extends. Cylindrical section 158 fits into a second opening of device 106. Projection 160 extends from enlarged disc 156 in the opposite direction from cylindrical section 158. Projection 160 provides for attachment of tubing 118.

Passageway 162 provides fluid communication from the end of projection 160 to the inside of cylindrical section 158. Fasteners 164 are used to further secure the supports 116, 120 to device 106. If device 106 is somewhat elastic, tension from the device 106 can help hold device 106 on the supports 116, 120. The flow region 166 is the portion of inside of the device between supports 116, 120.

FIG. 6 depicts another embodiment of the support system used to interface fluid conduits 102 with device 106. In this embodiment, first support 116 is used as shown in FIG. 2. Second ring support 170 replaces second support 120. Second ring support 170 has comparable structure to first support 116.

Another embodiment of the support system is depicted in FIGS. 7 and 8. The support system includes a cone section 172 attached to tubing 114 and a cone section 174 attached to tubing 118. Cone section 172 is inserted into an opening in the device 106 and secured adjacent to the leaflets 130. Cone section 174 is inserted into the opposite opening in the device 106 and placed between commissures 176 adjacent to the leaflets 130. Cone sections 172 and 174 preferably are placed such that leaflets 130 do not contact cone sections 172, 174 during motion of leaflets 130 due to fluid flow.

The elastic property of device 106 assists with placement of the support system in the vicinity of the leaflets. The cone sections can be secured by the tension against device 106. Clamps 178 around the appropriate parts of device 106 can provide additional help in securing cone sections 172, 174. Attachment of the support system near the leaflets 130 create a smaller flow region.

An alternative embodiment of the fluid conduit system 200 is depicted in FIGS. 9–11. A dual flow support 202 is attached to a one way flow device 204. Device 204 includes leaflets 206 that inhibit flow from top 208 of device 204 out the bottom 210 of device 204, although some leakage through the leaflets is possible. Device 204 further includes commissures 212 that direct the flow of fluid within flow region 214.

An inflow conduit 216 and an outflow conduit 218 are attached to dual flow support 202. Inflow conduit is in fluid communication with liquid source 220. Outflow conduit 218 is in fluid communication with collection reservoir 222. Collection reservoir 222 includes a vent 224. Liquid from liquid source 220 flows through inflow conduit 216 through the flow region 214 and out through outflow conduit 218 into collection reservoir 222. Liquid source 220 and/or collection reservoir 222 optionally can be connected to one or more pumps 226 to supply or remove liquid as appropriate. Referring to FIG. 12, plug 228 can be secured to the bottom 210 of device 204 to prevent liquid applied to the tissue exterior from entering bottom 210 of device 204. Rather than using plug 228, a skirt 230 (FIG. 13) can be attached to bottom 210 to divert liquid applied to the tissue exterior from entering bottom 210.

Referring to FIG. 14, an alternative embodiment of the apparatus 300 includes fluid conduit system 302, fluid applicator 304 and medical device 306. Apparatus 300 can be used with any vascular tissue or device 306 that includes a definable flow region. Fluid conduit system 302 has a similar structure as fluid conduit system 102 of apparatus 100. Fluid conduit system 302 includes a peristaltic pump 308 connected with fluid communication to a first fluid source 312 and to a first support 316. In this embodiment, the equivalent to tubing 118 of apparatus 100 is absent. Fluid flowing from second support 320 falls into a basin 322. Second support 320 can have a reduced outflow cross section to allow device 306 to fill up with the first fluid from source 312.

Fluid applicator 304 includes a container 326 holding a second fluid. Container 326 is in fluid communication with peristaltic pump 328. Pump 328 is in fluid communication with a sprayer 330 with an intervening solenoid valve 332 between pump 328 and sprayer 330. Solenoid valve 332 can be used to pulse the flow of fluid to sprayer 330.

Referring to FIGS. 14–17, sprayer 330 is cylindrically shaped. Sprayer 330 has a cylindrically shaped cavity 334. Cavity 334 is in fluid communication with port 336 for connection with the fluid source from solenoid valve 332. Cavity 334 is connected to a spray director 338 having a plurality of spray holes 340.

Spray director 338 is a cylindrical shaped. Spray holes 340 preferably are small enough that liquid does not leak from the holes when no liquid pressure is applied by way of port 336. The spray holes preferably have a diameter from about 0.2 mm to about 3.2 mm. When pressure is applied from the port 336, liquid is directed in a spray through the spray holes 340.

Figure 16:
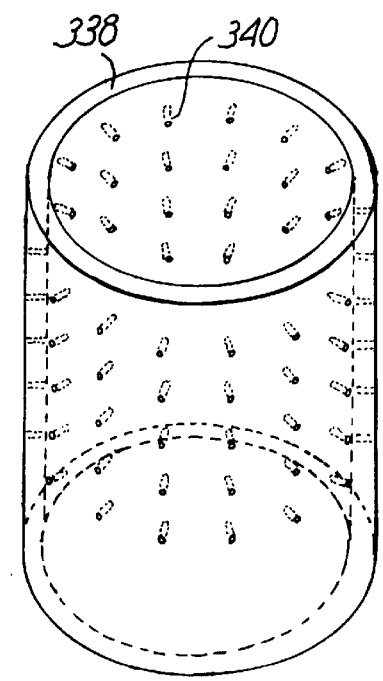
FIG. 16 is a perspective view of the sprayer of FIG. 15.

Spray holes 340 can be oriented to direct the desired spray to cover the desired portion of device 306. As depicted in FIG. 16, the spray holes 340 are oriented radially. Alternatively, the spray holes can be oriented at an angle relative to the radial direction. The number and size of spray holes 340 can be selected to spray the desired quantity of liquid at the pressure produced by pump 328. In alternative embodiments, the sprayer and/or spray director can have noncylindrical shapes as appropriate for the desired spray pattern.

Referring to FIG. 18, an alternative embodiment of the apparatus 400 is designed for the differential treatment of a sheet shaped medical device 402. Frames 404, 406 are clamped over the medical device 402 to assist with maintaining the first fluid 408 and the second fluid 410 on their respective sides of the sheet. Clamps 412, 414 are used to secure frames 404, 406 over or around medical device 402. A variety of designs can be used for clamps 412, 414, the number of clamps can be altered as desired. Alternatively, frames 404, 406 can incorporate integral fasteners obviating the need for clamps 412, 414.

The first fluid applicator is a liquid container 416 located adjacent frame 404. The second fluid applicator is a liquid container 418 located adjacent frame 406. Frames 404, 406 have openings 420, 422, respectively. Openings 420, 422 permit contact of fluids 408, 410 with opposite sides of medical device 402. Frames 404, 406 prevent significant commingling of fluids 408 and 410. In alternative embodiments, one or both of fluid applicators 416, 418 can direct a spray of liquid, gas or combination thereof at the appropriate surface of medical device 402.

Fluids

The first fluid and/or second fluid can be an active fluid. Preferably, a fluid is counteractive with respect to other fluids, if active, being used. A counteractive fluid inhibits or counteracts the active properties of the other fluid or fluids. A counteractive fluid can act, for example, by dilution, pH adjustment, ionic strength adjustment, reaction with an active ingredient and alteration of the solubility of an active ingredient. A fluid can function as a counteractive fluid through application of the fluid at a temperature that inactivates another active fluid. As a specific example, an active fluid can include a $AlCl_3$ solution that provides an anticalcification treatment for certain tissues, and the corresponding counteractive fluid can be a solution buffered at an approximately neutral pH where $AlCl_3$ is substantially insoluble.

A fluid can be active by way of compositions within the fluid and inactivating with respect to other active fluids. Alternatively, the counteractive fluid can be inert (not active) with respect to the medical device. An inert, counteractive fluid can be purified water or, preferably, an aqueous buffer that has a physiological pH from about 6 to about 8, and more preferably about 6.3 to about 7.5. Suitable buffers can be based on, for example, the following compounds: phosphate, borate, bicarbonate, carbonate, cacodylate, citrate, and other organic buffers such as tris (hydroxymethyl)aminomethane (TRIS), N-(2-hydroxyethyl) piparazine-N'-(2-ethanesulfonic acid) (HEPES) or morpholine propanesulphonic acid (MOPS). The ionic strength of the inert, counteractive fluid can be adjusted by the addition of one or more inert salts including, for example, NaCl and KCl. Preferably, the ionic strength is near physiological values for the treatment of natural tissues. Ringer's solution can be used to provide appropriate buffering and ionic strength.

As already noted, one or both of the first and second fluids can be an active, i.e., a treatment fluid, that includes one or more surface modifying compositions. If both the first and second fluids are treatment fluids, they generally are different treatment fluids. Appropriate surface modifying compositions include, for example, antimicrobial compositions, anticalcification compositions, fixation compositions, decellularization compositions, growth factors, antithrombics, cell adhesion molecules and other chemotactants. Chemotactants can alter host responses with respect to healing, immunogenicity and thrombogenicity. Treatment fluids can also include a solvent, buffer, inert salts and other compositions that do not significantly modify the device.

Potential calcification inhibitors include, for example, alcohols, toluidine blue, diphosphates and detergents such as sodium dodecyl sulfate and alpha amino oleic acid. Also, certain polyvalent metal cations, including $Al^{+3}$, $Mg^{+2}$ and $Fe^{+3}$, have been found to inhibit calcification. Other metal cations have antimicrobial activity, such as ions of Ag, Au, Pt, Pd, Ir, Cu, Sn, Sb, Bi and Zn. A variety of other compositions can provide antimicrobial activity including certain fixation compositions and antibiotics such as penicillin.

Fixation stabilizes the tissue, especially from enzymatic degradation, and reduces antigenicity. Some popular fixation agents act by chemically crosslinking portions of the tissue, particularly collagen fibers. Crosslinking compounds include a variety of organic compounds typically with two or more functional groups. Particularly preferred crosslinking compounds include diamines, epoxies, dialdehydes, dimediated photo oxidation, other oxidative crosslinking agents and formaldehyde, which is capable of acting difunctionally. Preferred dialdehydes include, for example, glutaraldehyde, malonaldehyde, glyoxal, succinaldehyde, adipalaldehyde, phthalaldehyde and derivatives thereof. Derivatives of glutaraldehyde include, for example, 3-methylglutaraldehyde and 3-methoxy-2,4-dimethyl glutaraldehyde. Differential treatment can be used to apply one fixation agent for part of the device and another fixation agent for another portion of the device. This differential fixation can maximize the benefit of each technology and improve device performance.

Another approach to reducing calcification of bioprostheses involves decellularizing the tissue since nonviable cells in transplant tissue are sites for calcium deposition. Various approaches have been developed for removing nonviable cells from tissue. Some of these methods are based on detergent treatments. Other methods use enzymes such as deoxyribonucleases or ribonucleases, sometimes combined with nonionic and/or anionic detergents.

Some recent, promising methods are based on the use of lipases combined with other enzymes and, optionally, detergents. See, for example, WO 9603093A and WO 9632905A, incorporated herein by reference. Treatment with hypotonic and/or hypertonic solutions, which have nonphysiological ionic strengths, can promote the decellularization process. These various decellularization solutions generally are suitable as treatment solutions. Proteases also can be used effectively to decellularize tissue.

The treatment conditions, however, to decellularize thick and compacted tissue generally is incompatible with more delicate membrane like tissue. Differential treatment of these tissues can decellularize the respective tissues under conditions suitable for each tissue. The decellularization can be performed in stages with some or all of the stages involving differential treatments. For example, a potent mixture of proteases, nucleases and phospholipases could be used in high concentrations to decellularize the aortic wall while a protective solution is circulated through the inner portion of the valve. This protective solution could be selected such that it would inactivate the mixture of enzymes in the first solution if the first solution comes in contact with the inner region through leakage. This inactivation could be accomplished by circulating cold solutions through the inner region to inhibit enzyme activity or by including appropriate enzyme inactivator(s) in the circulating solution. Following successful decellularization of the aortic root, a more gentile enzyme solution appropriate for leaflet decellularization could be circulated through the inner region.

The treatment solutions can be prepared at concentrations appropriate for the method of application and the type of solution. Treatment times similarly can be adjusted based on the concentration and the conditions used for application. Optimization may be desirable or necessary.

Additional Treatments

The medical devices can be treated with other surface modifying compositions either prior to or following the differential treatment. For example, a final sterilization can be performed prior to storage of the device. Similarly, several differential treatments can be applied to the same medical device. The several differential treatments can involve multiple differential treatments of the same two portions of the device or differential treatments with respect to different portions of the device.

A differentially treated device can be placed in a package along with packing material and appropriate labeling for distribution. Additional sterilization can take place following packaging, for example using radiation. The devices are distributed to medical personnel responsible for the care of the patient to be treated with the device. The device can be rinsed in sterile saline solution prior to administration by medical personnel.

EXAMPLES

Example 1

This example demonstrates the feasibility of applying an anticalcification agent under harsh conditions without damaging the leaflets of a porcine aortic heart valve.

Two aortic porcine valves were cleaned in 0.9 percent saline, prepped and mounted as shown in FIGS. 2 and 14. One valve was sutured to distinguish it from the other valve. Both bioprosthetic valves were crosslinked in 1300 ml of citrate buffered 0.5 percent glutaraldehyde solution in a single 1500 ml beaker for 118 hours. During crosslinking, a slight backpressure was applied against the leaflets. After crosslinking the mounting ties were replaced due to slight shrinkage of the bioprosthetic valve to ensure a tight seal.

Then, the valves were placed in an apparatus as depicted in FIG. 1. The device and supports were placed in a 2000 ml beaker. A HEPES buffered 80 percent ethanol solution with about 0.0005 percent by weight of congo red indicator was pumped forward through the bioprosthetic valves from two 400 ml reservoirs. Once adequate flow was established through the valves, 1900 ml of 0.1 M aluminum chloride solution was added to the 2000 ml beaker.

The congo red indicator indicated that the sutured iopros-thetic valve had a small leak below the suture. A ark red streak indicated leakage through the bioprosthesis into the buffered ethanol line. The second, non-sutured valve did not leak substantially. After about 2 hours the bioprosthetic valves were removed and rinsed with 0.9 percent saline.

Following removal from the aluminum solution and rinsing, four 8 mm root punches and all three leaflets were removed from each bioprosthetic valve. The root punches were taken two from either side of the leaflets. The samples were hydrolyzed with 70 percent $HNO_3$ and analyzed for aluminum, calcium and phosphorous by ICP-AES (Inductively Coupled Plasma-Atomic Emission Spectroscopy) using an Thermo Jarrell Ash Atom Scan 16 apparatus (Thermo Jarrell Ash Corp., Franklin, Mass.). An acid blank control was used to compensate for aluminum that is present in the glassware. The results of the ICP-AES measurements are found in Table 1.

TABLE 1

|  | Weight | Aluminum | | Calcium | | Phosphorous | |
| --- | --- | --- | --- | --- | --- | --- | --- |
|  |  | ppm | mg/g | ppm | mg/g | ppm | mg/g |
| Root |  |  |  |  |  |  |  |
| 1 (S) | 31.30 | 4.63 | 3.70 | 0.09 | 0.07 | 2.36 | 1.88 |
| 2 (S) | 25.70 | 3.52 | 3.43 | 0.04 | 0.04 | 1.42 | 1.38 |
| 3 (S) | 17.70 | 3.77 | 5.32 | 0.05 | 0.07 | 1.41 | 1.98 |
| 4 (S) | 26.80 | 3.53 | 3.95 | 0.06 | 0.06 | 1.52 | 1.70 |
| 1 (NS) | 36.60 | 3.67 | 2.51 | 0.11 | 0.07 | 1.91 | 1.31 |
| 2 (NS) | 19.70 | 3.12 | 3.96 | 0.09 | 0.11 | 1.93 | 2.45 |
| 3 (NS) | 25.40 | 4.86 | 4.78 | 0.10 | 0.10 | 2.55 | 2.51 |
| 4 (NS) | 36.60 | 3.55 | 2.43 | 0.16 | 0.11 | 2.55 | 1.74 |
|  |  | Avg. = | 3.76 | Avg. = | 0.08 | Avg. = | 1.87 |
|  |  | St. Dev. = | 0.94 | St. Dev. = | 0.02 | St. Dev. = | 0.41 |
| Leaflet |  |  |  |  |  |  |  |
| 1 (S) | 13.70 | 0.17 | 0.30 | 0.05 | 0.08 | 0.93 | 1.69 |
| 2 (S) | 8.10 | 0.13 | 0.41 | 0.02 | 0.05 | 0.54 | 1.67 |
| 3 (S) | 14.30 | 0.10 | 0.17 | 0.01 | 0.02 | 0.55 | 0.97 |
| 1 (NS) | 10.50 | 0.07 | 0.17 | 0.04 | 0.10 | 0.74 | 1.76 |
| 2 (NS) | 6.00 | 0.10 | 0.42 | 0.02 | 0.08 | 0.45 | 1.89 |
| 3 (NS) | 11.80 | 0.11 | 0.24 | 0.06 | 0.12 | 0.89 | 1.89 |
|  |  | Avg. = | 0.29 | Avg. = | 0.07 | Avg. = | 1.65 |
|  |  | St. Dev. = | 0.10 | St. Dev. = | 0.03 | St. Dev. = | 0.31 |
| Acid Blank Controls |  | 0.058–0.07 |  |  |  |  |  |

S = Valve 1 - sutured
NS = Valve 2 - non-sutured

Inspection of the results reveals slightly reduced average aluminum loading (3.76 mg Al/g tissue) of the root tissue and greatly reduced average aluminum loading (0.29 mg Al/g tissue) of the leaflets when compared to current treatment methods (5–8 mg Al/g tissue).

Example 2

The following example demonstrates the effective application to the root of aortic porcine valves of aluminum salt as an anticalcific using a spray applicator without treatment of the leaflets.

To prepare the aluminum salt solution, 965.6 g $AlCl_3$-$6H_2O$ (Lot No. 65H0328 from Sigma Chemical) was mixed with 10 liters (L) water purified with a reverse osmosis purifier (RO water). This mixture was diluted to 40 L with RO water to produce an approximately 0.1 M $AlCl_3$ solution. A buffered saline solution was prepared by combining 233.6 g NaCl (Lot No. 912944, Fisher Scientific) with 476.8 g HEPES free acid (Lot No. F12723, Sigma Chemical) in 40 L RO water. Sodium hydroxide (Lot 914743A, Fisher Scientific) was added to adjust the pH of the buffered saline to 7.4±0.1.

A HEPES buffered saline solution was prepared by adding 9.28 g NaCl (Lot 964733 from Fisher) followed by 19.06 g HEPES free acid (Lot 75H5716) to 1 L RO water and mixing. Then, 8420 ml of 95 percent undenatured ethanol was added. After addition of the ethanol, 1000 ml RO water was added to produce a solution with 10 L volume. The pH was adjusted to 7.45 by adding approximately 2 g NaOH (Lot 914743A, Fisher) and 20 ml 1.0N HCl.

Two aortic porcine valves (valves A and B) were obtained. These were fixed in citrate buffered, 0.5 percent glutaraldehyde for 6 days. During fixation, a 2 mmHg coaptive pressure was applied across the leaflets in a backflow direction.

Next, valves A and B were treated differentially with the aluminum chloride solution and the buffered saline. First, valve A was placed into 500 ml 0.9 percent saline for 15 minutes. The saline was decanted off, and the valve was immersed with another 500 ml saline for 15 minutes. The valve was removed from the saline and placed on supports as shown in FIG. 2. After attachment to the supports, valve A was placed within a sprayer as shown in FIGS. 14–17. The sprayer had dimensions of about 3.5 in×3.5 in×3.5 in, and the spray director had a pores with a diameter of 0.03125 in. The sprayer was primed with the aluminum solution for 2 minutes to fill the cavity with solution.

Following priming of the sprayer, flow of HEPES saline was started through the conduit system. A smaller support cross section on the outflow yielded a flow rate of 3.0 L/hr from the lower support. About 10 inches of buffered HEPES was maintained in the conduit system above valve A. Valve A leaked HEPES buffer from coronary arteries at a rate of 0.2 L/hr for a total flow rate including flow from the lower support of 3.2 L/hr.

With the HEPES buffer flowing the sprayer was pulsed with the 0.1 M $AlCl_3$ solution to produce a total flow of about 18 l/hr. The sprayer was pulsed 1 sec. on followed by 4 sec. off. The differential treatment was continued for 1 hour. Following treatment valve A was removed from the sprayer and placed in 500 ml HEPES saline for 30 secs. Treatment was repeated for valve B. Considerably less HEPES saline leaked from the coronary arteries of valve B with approximately 53 ml/min (3.2 L/hr) flowing through the lower support as intended.

Following treatment, both valves A and B were placed in separate 150 ml HEPES buffered 0.5 percent glutaraldehyde for 21.5 hrs in a sterile laminar flow hood. Then, two samples were taken from each valve. One sample was a leaflet (A1L and B1L) and the second sample was a 8 mm root punch (A1R and B1R). The four samples were lyophilized for 24 hrs. Then, the samples were hydrolyzed using 1 ml 70% $HNO_3$ (Lot 116030, Fisher) per sample. The hydrolyzed samples were analyzed for Al content as described in Example 1.

Following treatment with aluminum chloride and HEPES buffer, valves A and B further were treated with buffered ethanol. First, valves A and B together were placed in 800 ml HEPES buffered saline for 10 min. The HEPES buffered saline was decanted off and replaced with another 800 ml of HEPES buffered saline. The valves were kept in this second solution of HEPES buffered saline for 15 minutes. The solution again was decanted off and replaced the 800 ml HEPES buffered 80 percent ethanol solution. After 10 minutes, the buffered ethanol was decanted off and replaced with another 800 ml of HEPES buffered ethanol. After 1440 min, the second HEPES buffered saline solution was decanted off and replaced with 800 ml of HEPES buffered saline. The HEPES buffered saline was replaced after 10 minutes, and the valves were kept in the second HEPES buffered saline solution for 1440 min.

Then, the valves were removed from the solution. Two additional samples were made for each valve (A2L, A3L, B2L and B3L) by removing the remaining leaflets. Four 8 mm root punches were taken from each valve. These root punches were split with a scalpel to form an interior root punch (A2RI–A5RI and B2RI–B5RI) and an exterior root punch (A2RO–A5RO and B2RO–B5RO). Splitting the root punches creates samples that can provide information on the gradient of aluminum loading across the root. These twenty samples were lyophilized, hydrolyzed and analyzed, as described for the samples prior to ethanol treatment.

Figure 19:
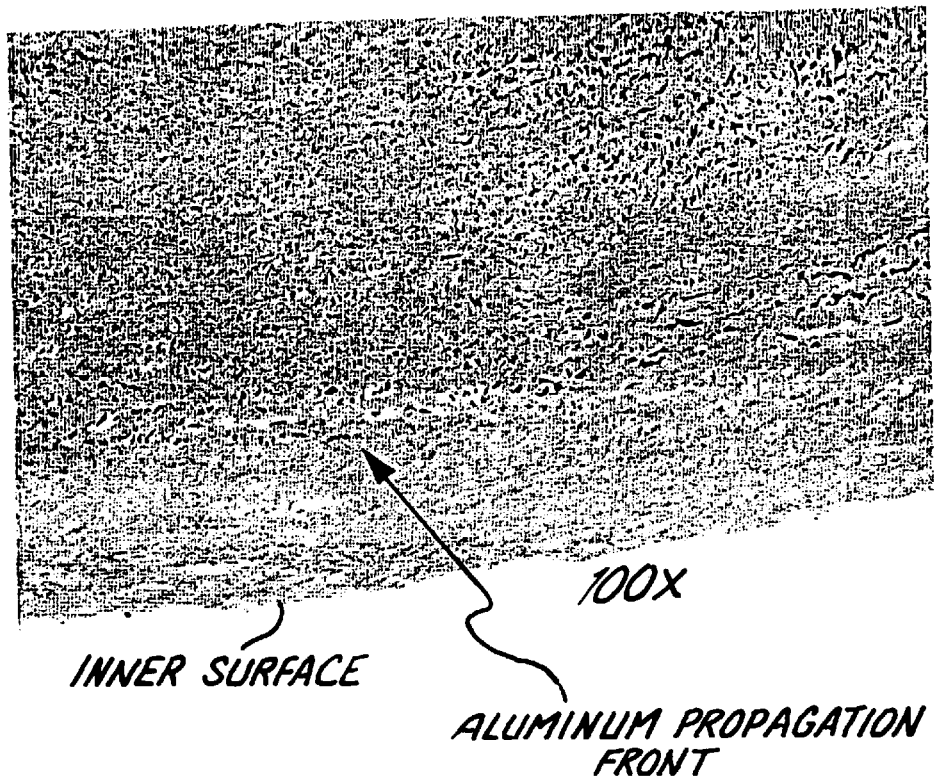
FIG. 19 is a representation of a photomicrograph of a histological section of a porcine aortic wall section that has been treated differentially with aluminum.

The results of the aluminum analysis for all of the samples of Example 2 are shown in Table 2. These results demonstrate that little aluminum is deposited on the leaflets. Furthermore, there is a considerable gradient in aluminum loading across the root. This can be seem visually in the 100 X micrograph of FIG. 19 showing a histological section of the differentially treated valve treated with a stain specific for aluminum. The darker region shows the aluminum loading in the outer portion of the tissue covering a majority of the thickness of the tissue while the inner portion is free of aluminum loading.

TABLE 2

| Before Ethanol Treatment: | | After Ethanol Treatment: | | |
|---|---|---|---|---|
| Leaflets: | Root: | Leaflets: | Root Interior: | Root Exterior: |
| 0.18 (A1L) | 2.50 (A1R) | 0.16 (A2L) | 0.32 (A2RI) | 5.31 (A2RO) |
| 0.18 (B1L) | 2.39 (B1R) | 0.19 (A3L) | 0.08 (A3RI) | 4.33 (A3RO) |
| | | 0.10 (B2L) | 0.03 (A4RI) | 3.87 (A4RO) |
| | | 0.16 (B3L) | 0.08 (A5RI) | 3.99 (A5RO) |
| | | | 0.15 (B2RI) | 3.01 (B2RO) |
| | | | 0.61 (B3RI) | 2.65 (B3RO) |
| | | | 0.51 (B4RI) | 5.65 (B4RO) |
| AVG. | | | 0.12 (B5RI) | 4.92 (B5RO) |
| 0.18 | 2.44 | 0.15 | 0.24 | 4.22 |

Other embodiments of the invention are within the scope of the claims.

What is claimed is:

1. An apparatus comprising:
   (a) a first fluid applicator comprising a reservoir of a first fluid, said first fluid applicator contacting said first fluid with a first portion of a medical device; and
   (b) a second fluid applicator comprising a reservoir of a second fluid, said second fluid applicator contacting said second fluid with a second portion of said medical device, said second fluid applicator applying said second fluid in effective isolation from said first portion of said medical device and said first fluid applicator applying said first fluid in effective isolation from said second portion of said medical device.

2. The apparatus of claim 1 wherein said first fluid applicator comprises a fluid conduit system including a support system for attaching said fluid conduit system to said medical device such that when attached to said device, fluid flowing through said conduit system contacts a flow region of said medical device.

3. The apparatus of claim 2, wherein said support system comprises a support that inserts within an opening in said medical device, said support having a passageway such that fluid flowing through said conduit system flows through said passageway and contacts said first portion of said medical device.

4. The apparatus of claim 3, further comprising a fastener that holds said medical device against said support.

5. The apparatus of claim 1, wherein said first fluid is selected from the group consisting of a liquid bath, a liquid spray, an aerosol and a gas.

6. The apparatus of claim 1, wherein said second fluid is selected from the group consisting of a liquid bath, a liquid spray, an aerosol and a gas.

7. The apparatus of claim 2, wherein said second fluid applicator comprises a container for holding a fluid into which said medical device attached to said conduit system is immersed, said conduit system effectively isolating said first region from said second region.

8. The apparatus of claim 2, wherein said second fluid applicator comprises a sprayer that directs streams of liquid at said medical device attached to said conduit.

9. The apparatus of claim 1, further comprising a frame that holds a sheet section of a medical device to facilitate said application of said second fluid in effective isolation from said first portion of said medical device, said first portion being one side of said sheet section, and said second portion being located on the opposite side of the plane defined by said frame from said first portion.

10. The apparatus of claim 9, wherein said second portion is a side of said sheet opposite said first portion.

11. The apparatus of claim 1 wherein said medical device comprises tissue.

12. The apparatus of claim 11 wherein said tissue has a tubular shape.

13. The apparatus of claim 12 wherein said medical device further comprises leaflets.

14. The apparatus of claim 1 wherein said medical device comprises leaflets, said leaflets comprising tissue.

15. The apparatus of claim 1 wherein said medical device is a heart valve prosthesis.

16. The apparatus of claim 14 wherein said medical device comprises a vascular graft.

17. The apparatus of claim 14 wherein said first fluid applicator comprises a fluid conduit. System including a support system for attaching said fluid conduit system to said medical device such that when attached to said device, fluid flowing through said conduit system contacts a flow region of said medical device.

18. The apparatus of claim 17 wherein said second fluid applicator comprises a sprayer that directs streams of liquid at said medical device attached to said conduits.

19. The apparatus of claim 1 wherein said first fluid comprises a first fixation agent and said second fluid comprises a second fixation agent.

20. The apparatus of claim 1 wherein said first fluid comprises an anticalcification agent and said second fluid comprises a buffer with a pH from about 6 to about 8.

* * * * *

UNITED STATES PATENT AND TRADEMARK OFFICE
CERTIFICATE OF CORRECTION

PATENT NO. : 6,132,473 Page 1 of 1
DATED : October 17, 2000
INVENTOR(S) : Williams et al.

It is certified that error appears in the above-identified patent and that said Letters Patent is hereby corrected as shown below:

Title page, item [56],
References Cited FOREIGN PATENT DOCUMENTS, add the following: --
| | | |
|---|---|---|
| 0 281 736 A1 | 9/1998 | European Pat. Off. |
| 0 507 722 A1 | 10/1992 | European Pat. Off. |
| GB 1 510 163 | 5/1978 | Great Britain |

Column 16,
Line 24, change ". System" to -- system --.

Signed and Sealed this

Second Day of October, 2001

Attest:

NICHOLAS P. GODICI
Attesting Officer  Acting Director of the United States Patent and Trademark Office